US008777006B2

(12) United States Patent
Jatana et al.

(10) Patent No.: US 8,777,006 B2
(45) Date of Patent: Jul. 15, 2014

(54) PATTY MANAGER AND METHOD

(75) Inventors: Sanjay Jatana, Lone Tree, CO (US); Scott A. Comeaux, Castle Rock, CO (US)

(73) Assignee: Clear Solutions LLC, Castle Rock, CO (US)

( * ) Notice: Subject to any disclaimer, the term of this patent is extended or adjusted under 35 U.S.C. 154(b) by 1558 days.

(21) Appl. No.: 11/506,533

(22) Filed: Aug. 18, 2006

(65) Prior Publication Data

US 2007/0062835 A1 Mar. 22, 2007

Related U.S. Application Data

(60) Provisional application No. 60/719,672, filed on Sep. 22, 2005.

(51) Int. Cl.
*A61B 19/02* (2006.01)
(52) U.S. Cl.
USPC ............................ 206/440; 206/363; 206/570
(58) Field of Classification Search
USPC ......... 206/440, 370, 570, 339, 438, 363, 456, 206/63.5, 572, 388, 441, 372
See application file for complete search history.

(56) References Cited

U.S. PATENT DOCUMENTS

| | | | | |
|---|---|---|---|---|
| 1,365,682 A * | 1/1921 | Greist et al. | | 206/373 |
| 2,110,572 A | 3/1938 | Foote | | |
| 3,481,462 A | 12/1969 | Chapel | | |
| 3,948,390 A | 4/1976 | Ferreri | | |
| 4,008,802 A | 2/1977 | Freitag | | |
| 4,190,153 A * | 2/1980 | Olsen | | 206/362 |
| 4,415,089 A * | 11/1983 | Ruffa | | 211/85.13 |
| 4,494,653 A * | 1/1985 | Praderio | | 206/370 |
| 4,596,329 A | 6/1986 | Eldridge, Jr. | | |
| 4,637,513 A * | 1/1987 | Eldrige, Jr. | | 206/370 |
| 4,784,267 A | 11/1988 | Gessler et al. | | |
| 4,832,198 A | 5/1989 | Alikhan | | |
| 4,887,715 A * | 12/1989 | Spahn et al. | | 206/370 |
| 4,889,230 A * | 12/1989 | Zachry | | 206/362 |
| 4,903,837 A | 2/1990 | Duello | | |
| 4,966,595 A * | 10/1990 | Meringola et al. | | 604/393 |
| 5,346,677 A * | 9/1994 | Risk | | 422/297 |
| 5,394,983 A * | 3/1995 | Latulippe et al. | | 206/370 |
| 5,433,929 A | 7/1995 | Riihimaki et al. | | |
| 5,505,916 A * | 4/1996 | Berry, Jr. | | 422/300 |
| 5,947,286 A * | 9/1999 | Chau | | 206/372 |
| 6,012,580 A * | 1/2000 | Peters et al. | | 206/470 |
| 6,622,861 B2 * | 9/2003 | Kissling | | 206/362 |
| 6,896,136 B2 * | 5/2005 | Hu | | 206/378 |
| 6,945,546 B2 * | 9/2005 | Guirlinger | | 280/47.19 |
| 2004/0040873 A1 | 3/2004 | Koseki | | |
| 2007/0084742 A1 * | 4/2007 | Miller et al. | | 206/438 |

FOREIGN PATENT DOCUMENTS

JP 2001224603 7/2001

\* cited by examiner

*Primary Examiner* — Anthony Stashick
*Assistant Examiner* — Robert Poon
(74) *Attorney, Agent, or Firm* — Holland & Hart LLP

(57) ABSTRACT

The present invention provides a patty manager having a dispensing tray including one or more dispensing regions for receiving surgical patties, and a recovery tray having a plurality of recovery regions for receiving surgical patties. Each dispensing region may include a dispensing indicia located, and each recovery region can include a recovery indicia, which may correspond to a substantially similar dispensing indicia of the dispensing tray. A string guide may be disposed about at least a portion of the dispensing regions for the organization and management of the patty strings. A gripping tool may further be coupled to one of the dispensing or recovery trays.

22 Claims, 3 Drawing Sheets

PATTY MANAGER AND METHOD

CROSS-REFERENCE TO RELATED APPLICATION

This application is related to and claims priority from U.S. Provisional Patent Application Ser. No. 60/719,672, filed on Sep. 22, 2005, entitled, "SURGICAL PATTY MANAGER AND MANAGEMENT METHOD," the entire contents of which is incorporated herein by reference.

STATEMENT REGARDING FEDERALLY SPONSORED RESEARCH OR DEVELOPMENT n/a

FIELD OF THE INVENTION

The present invention relates to the surgical devices and more particularly to a device and method for carrying and managing the dispensing and recovery of surgical patties.

BACKGROUND OF THE INVENTION

Surgeons often use surgical patties during surgery to absorb fluids at or around the surgical site. Surgical patties (also referred to herein as cottonoids) are typically constructed of an absorbent sponge-like material, such as cotton, and are shaped as squares or rectangles having a string affixed at one end. Surgical patties also typically incorporate a radio opaque marker so that patties can be detected using x-rays.

Surgical patties typically are packaged on a liner in packages that contain multiple patties. For example, a typical package might include ten cottonoid patties on a cardboard liner. A nurse in the surgical suite must prepare the patties for use by removing the patties from the packaging and placing the patties on some sort of delivery device, such as a towel, basin, back of their hand, etc., in order to present them to the requesting surgeon. This method of delivery is not efficient and leads to inconsistencies based on different nursing techniques or individual preferences.

Certainly, it is imperative that the patty usage during surgery be tracked so that the surgeon and surgical staff can insure that all patties have been recovered from the patient. However, once the patties are used, there is likewise no consistent method or device to aid in the recovery and disposal of the soiled patties. This can lead to loss of the patty and time, and necessitate expensive tests to locate and account for all patties. For example, a patient has to be exposed to x-ray radiation to locate a missing patty to be sure it was not inadvertently left behind in the patient. This is due to national safety and hospital quality standards.

It is therefore desirable to have a device and method to aid the dispensing and recovery of surgical patties in a matter which permits quick and ready identification of the quantity of unused patties as well as the quantity of soiled and recovered patties.

SUMMARY OF THE INVENTION

The present invention advantageously provides a patty manager generally including a dispensing tray and a recovery tray. The dispensing tray may include one or more dispensing regions for receiving surgical patties, where each dispensing region may include a patty retention element. Further, each dispensing region may include a dispensing indicia located therein. The patty manager of the present invention may also include a string guide disposed about at least a portion of the dispensing tray and/or one or more dispensing regions, where the string guide may include a first channel extending longitudinally along a portion of the dispensing tray, and a second channel disposed about at least a portion of the periphery of the dispensing tray for the organization and management of the patty strings.

A recovery tray may be provided that is movably coupled to the dispensing tray such that the recovery tray is able to fold over onto the dispensing tray into a folded configuration. The recovery tray may define a plurality of recovery regions for receiving surgical patties, and each recovery region may include a patty retention element. Moreover, each recovery region can include a recovery indicia located therein, which may correspond to a substantially similar dispensing indicia of the dispensing tray. The patty manager may also include a gripping tool coupled to either the dispensing or recovery trays, and may further provide a separator sheet positionable within at least a portion of the dispensing tray.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
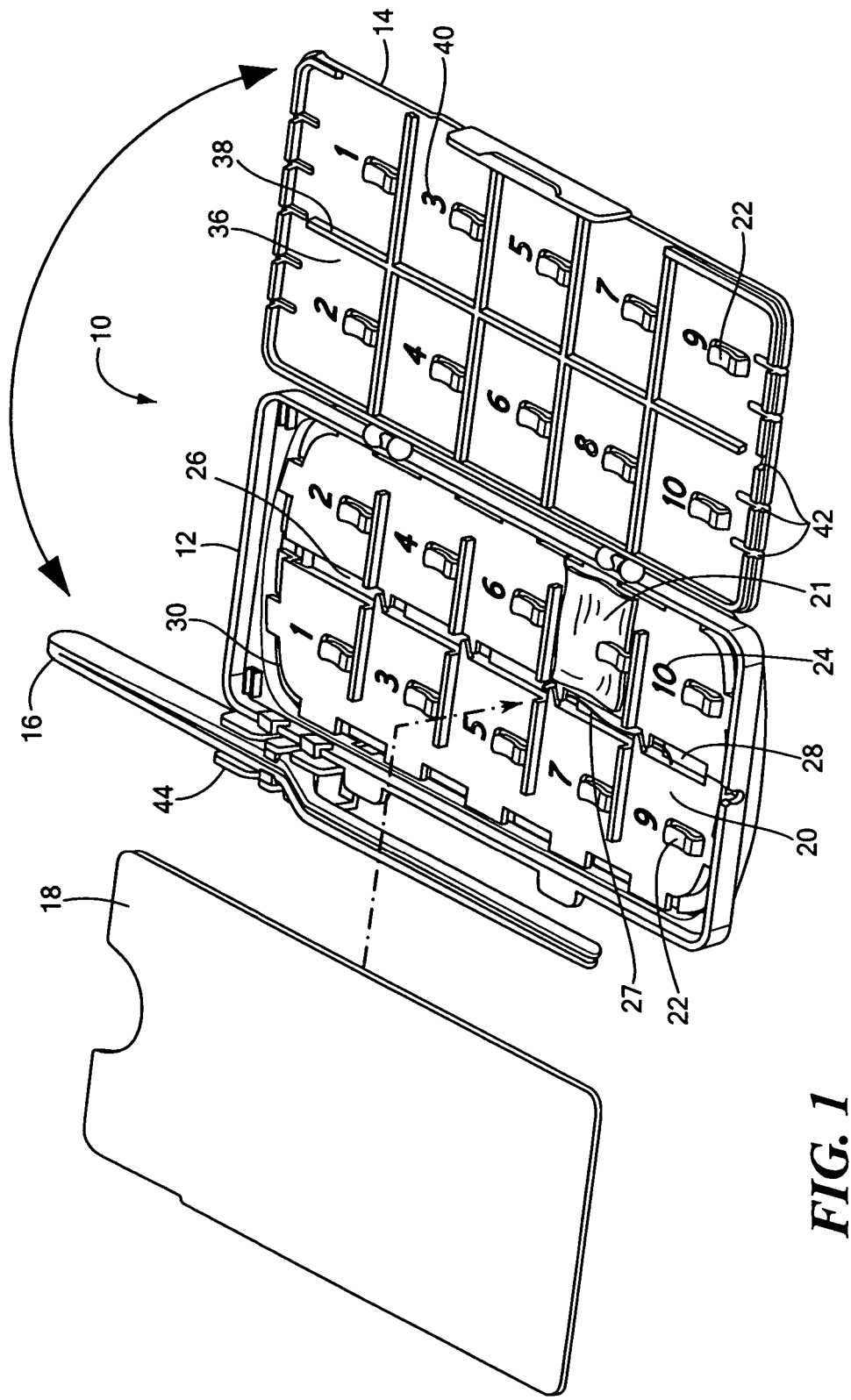
FIG. 1 illustrates an embodiment of a patty manager in accordance with the present invention.
Figure 2:
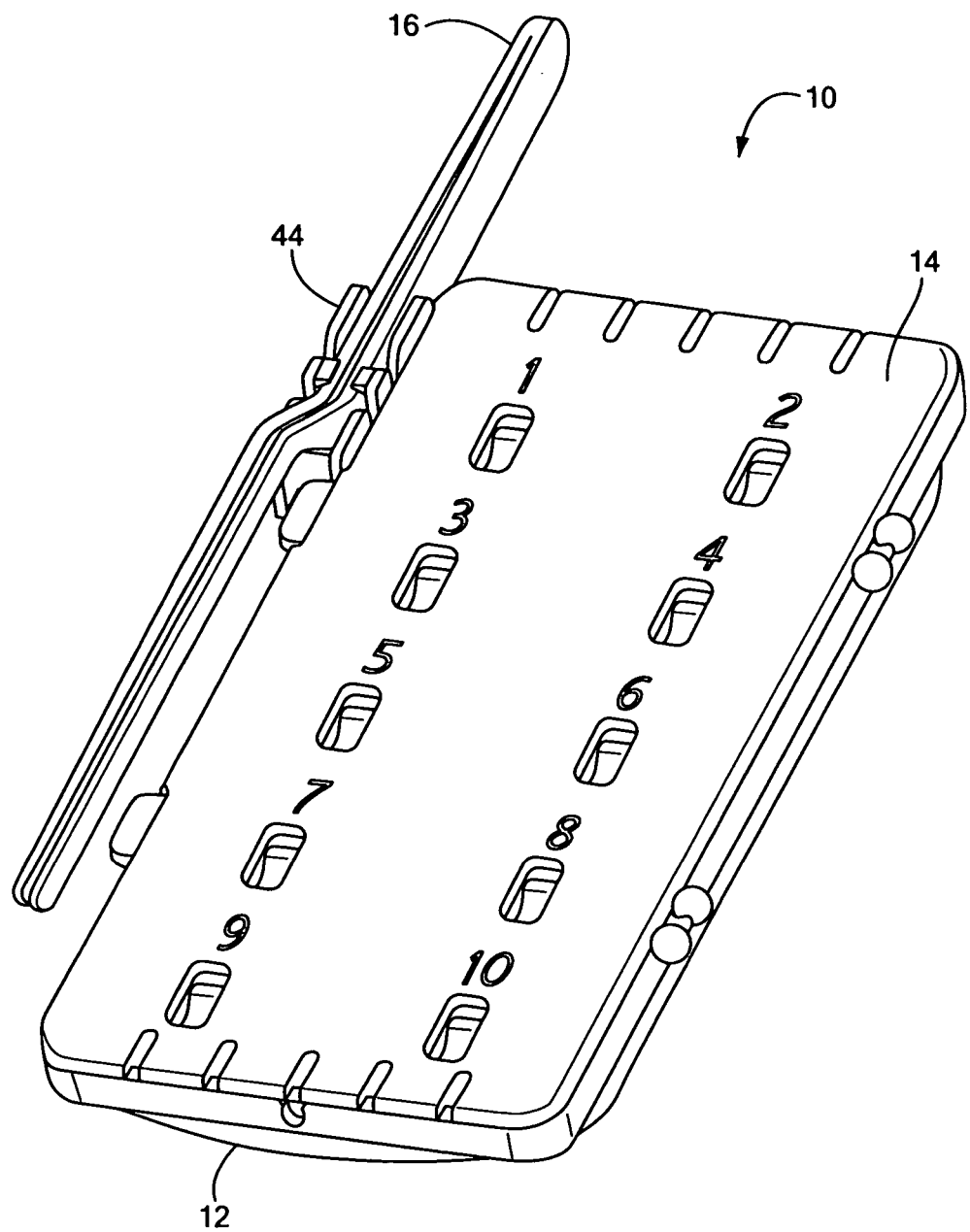
FIG. 2 shows an additional view of an embodiment of a patty manager in accordance with the present invention.

Referring now to the drawing figures in which like reference designators refer to like elements, there is shown in FIGS. 1 and 2, a surgical patty manager constructed in accordance with the principles of the present invention and designated generally as "10". Patty manager 10 may generally include a dispensing tray 12, a recovery tray 14, a gripping tool 16, and a separator sheet 18. The dispensing tray 12 and recovery tray 14 may be constructed from a readily disposable sterilizable polymer for ease of manufacturing and use.

The dispensing tray 12 may include one or more patty dispensing regions 20 for each of the quantity of patties 21 that patty manager 10 is intended to dispense. For example, FIG. 1 shows a patty manager 10 designed to accommodate ten surgical patties. Each patty dispensing region 20 may include a patty retention element 22 for releasably securing a surgical patty 21 to the patty dispensing region 20, and may include a variety of releasable coupling means, including mechanical couplings, adhesives, or the like. For example, the patty retention element 22 may include one or more protrusions, such as a tab protruding upward and inward toward a central area of dispensing region 20, where a surgical patty 21 may be positioned under the tab. In addition, the patty retention element 22 may be coupled to a portion of the dispensing tray 12 and/or dispensing region 20, and may further be molded as part of the dispensing tray 12.

Each patty dispensing region 20 may further include a dispensing indicia 24, which provides an indication of the quantity of surgical patties in use during a medical procedure. By viewing the dispensing indicia 24, surgical suite personnel can quickly determine how many patties are in use.

The patty manager 10 may further include a string guide 26 for guiding one or more patty strings 27 in an organized manner about the dispensing tray 12. The string guide 26 may include one or more channels disposed about at least a portion of the one or more dispensing regions 20 of the patty manager 10, and may further include a number of tabs or protrusions through which the patty strings may be routed. For example, the string guide 26 may include a first channel 28 extending down a longitudinal midline of the dispensing tray 12, and may further include a second channel 30 disposed around a peripheral portion of the one or more patty dispensing regions 20 of the surgical patty manager 10. Placement of the surgical patties in the dispensing regions 20 and subsequent routing of the patty strings through the string guide 26 reduce the likelihood that the strings may become entangled when the patties are dispensed. In use, the surgeon may select a patty 21 from the next dispensing region 20, and slide the patty 21 under the retention element 22 to remove it. As the patty 21 is being pulled, the patty strings 27 are guided through the string guide 26 in an organized fashion such that they do not get entangled with one another.

Figure 3:
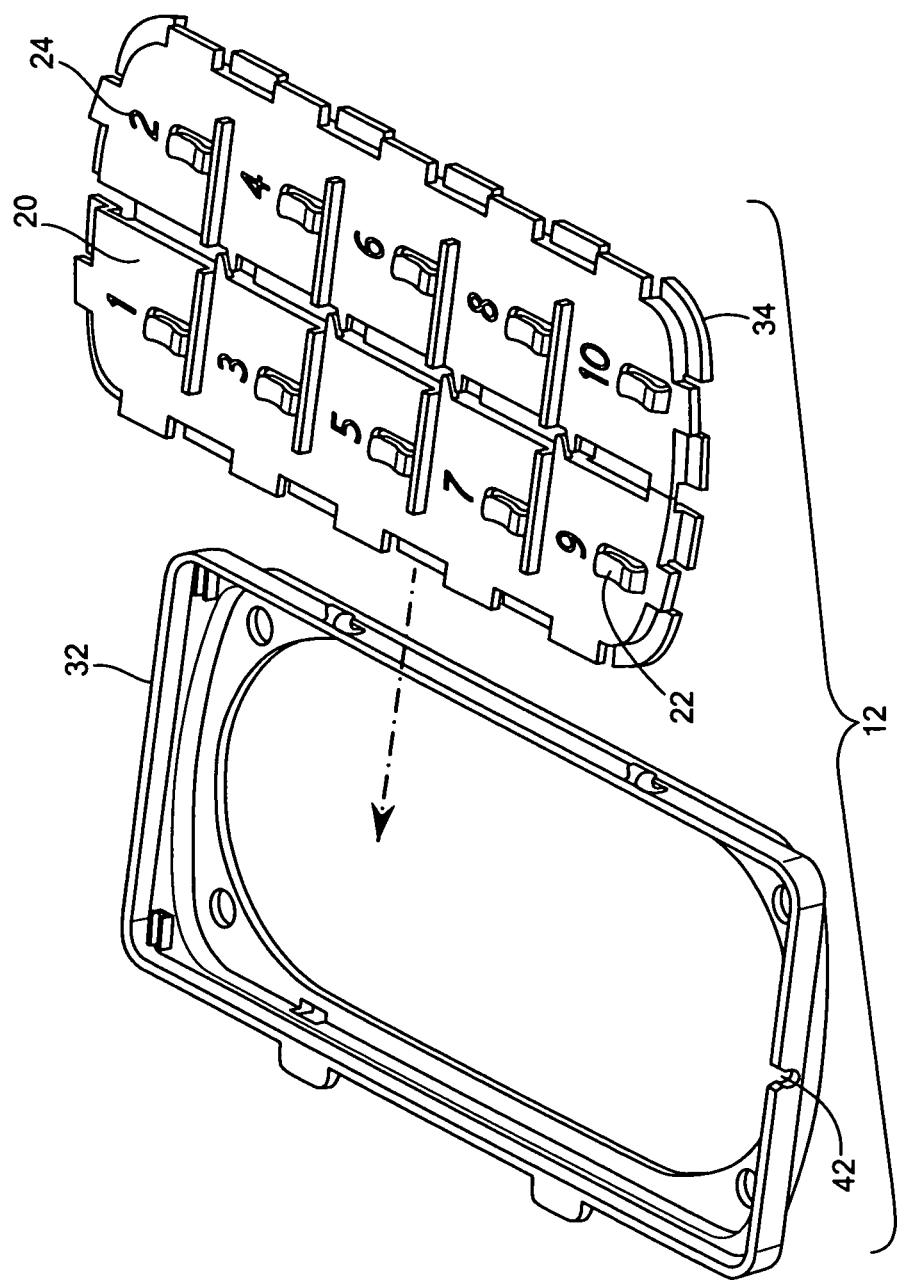
FIG. 3 provides yet another view of an embodiment of a patty manager in accordance with the present invention.

Of note, the dispensing tray 12 of the patty manager 10 may include a single piece that is molded or otherwise integrally formed to include the features described above. In addition, as shown in FIG. 3, the dispensing tray 12 may include a first portion 32 and a second portion 34, wherein the second portion 34 is releasably engageable with the first portion 32. The first portion 32 may form an outer shell or construct, where the second portion 34 is positionable within the first portion 32. The second portion 34 may include the one or more patty dispensing regions 20, patty retention elements 22, and at least a portion of the string guide 26 as described above. This two-part construction may ease the insertion of surgical patties for subsequent use and may further facilitate routing the strings of the surgical patties through the string guide 26.

Again referring to FIGS. 1 and 2, the patty manager 10 of the present invention may further include a recovery tray 14 movably coupled to the dispensing tray 12. The recovery tray 14 may be hingedly coupled to the dispensing tray 12 such that the recovery tray 14 is able to fold over onto the dispensing tray 12 into a folded configuration, and further, the recovery tray 14 and the dispensing tray 12 may be releasably engageable with one another. Such a folded configuration may facilitate packaging, shipping and disposal of the surgical patty manager 10. The recovery tray 14 may define a recovery region 36 for each surgical patty intended for use, and may correspond to the number of dispensing regions 20 of the dispensing tray 12. Each recovery region 36 may include one or more protrusions 38 about the periphery of the recovery region 36, including, for example, a longitudinal protrusion extending along a length of the recovery tray 14 and a transverse protrusion extending along a width of the recovery tray 14. In addition, similar to the dispensing tray 12, each recovery region 36 may include a patty retention element 22 for releasably securing a surgical patty thereto, as described above.

Each patty recovery region 36 may further include a recovery indicia 40, which provides an indication of the quantity of surgical patties recovered during a medical procedure. Each recovery indicia 40 on the recovery tray 14 may correspond to a substantially similar dispensing indicia 24 on the dispensing tray 12. When a patty 21 is inserted into a recovery region 36, it covers the recovery indicia 40 in that region. As such, surgical suite personnel can readily determine how many patties have been recovered by looking at the next viewable recovery indicia 40 of a subsequent recovery region 36. If the quantity of patties recovered added to the quantity of unused patties does not equal the starting quantities of patties, surgical suite personnel can quickly determine that a patty is unaccounted for.

In the event that patty manager 10 does not come preassembled with patties or if surgical suite staff does not wish to insert the patties and route the strings through string tabs prior to use, the periphery of the dispensing tray 12 and recovery tray 14 may include one or more spaces or apertures 42 which create an opening when the dispensing tray 12 and recovery tray 14 are in a folded, closed configuration. As such, the patty strings may be routed straight down through a central portion of the recovery tray 14 and through the openings created by spaces.

The surgical patty manager 10 of the present invention may further include a gripping tool 16 for removing and/or positioning surgical patties. The gripping tool 16 may include forceps removably affixed to the dispensing and/or recovery trays. Removable affixation may be achieved by the inclusion of a clip 44 or other fixation means as known in the art. The clip 44 may include one or more mounting tabs arranged to mate with a corresponding protrusion on the periphery of the recovery or dispensing tray 12. Moreover, the clip 44 may define an inner volume, formed by walls and a base arranged to accommodate a portion of the gripping tool 16. The clip 44 may include appropriate structure to retain and/or bias the gripping tool towards a closed position. As such, the griping tool 16 may be coupled to either of the trays with a surgical patty readily retained in the grasp of the gripping tool 16, thereby providing immediate access and availability when needed. Manufacturers and/or packagers may or may not choose to include a gripping tool 16 as part of the final product, as it is understood that the inclusion as part of the present invention is optional.

The patty manager 10 can also include a separator sheet 18. As can be seen, the separator sheet 18 can be provided to lay over the dispensing tray 12 to separate dispensing regions 20 from recovery regions 36. The separator sheet 18 can be made of paper, a thin polymer, etc., and may be sized to fit within or about a portion of the dispensing tray 12.

Of note, it is contemplated that patty manager 10 can be shipped from the point of manufacture with patties pre-inserted in dispensing tray 12 under tabs. It is also contemplated that surgical suite personnel can insert surgical patties under tabs at the time of surgery. Further, although patty manager 10 is shown in the drawing figures as supporting ten patties, the invention is not limited to such, as the patty manager 10 can be sized and arranged to support any quantity of patties of any given size.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A surgical patty manager for retaining a plurality of surgical patties, comprising:
   a first tray defining a dispensing region and a string guide, the dispensing region including a first plurality of patty retention elements adapted to retain unused surgical patties and a dispensing indicia associated with each of the first plurality of patty retention elements, and the string guide defining a channel extending longitudinally along a portion of the first tray and a protrusion extending partially over a portion of the string guide;

a plurality of unused surgical patties retained in the first plurality of patty retention elements, each of the unused surgical patties having an associated string routed through the string guide; and a second tray movably coupled to the first tray, the second tray defining a recovery region including a second plurality of patty retention elements adapted to receive used surgical patties and a recovery indicia associated with each of the second plurality of patty retention elements, each recovery indicia for the second plurality of patty retention elements having a corresponding dispending indicia associated with one of the first plurality of patty retention elements.

2. The surgical patty manager according to claim 1, wherein the dispensing region includes consecutively numbered dispensing identifiers associated with each of the first plurality of patty retention elements.

3. The surgical patty manager according to claim 2, wherein the recovery region includes consecutively numbered recovery identifiers associated with each of the second plurality of patty retention elements.

4. The surgical patty manager according to claim 3, wherein the consecutively numbered recovery identifiers correspond to the consecutively numbered dispensing identifiers.

5. The surgical patty manager according to claim 1, wherein the quantity of dispensing regions is equal to the quantity of recovery regions.

6. The surgical patty manager according to claim 1, wherein the second tray is hingedly coupled to the first tray, such that the second tray is able to fold over onto the first tray into a folded configuration.

7. The surgical patty manager according to claim 1, wherein the second tray is releasably engageable from the first tray.

8. The surgical patty manager according to claim 6, further comprising a separator sheet positionable between the first tray and the second tray when in the folded configuration.

9. The surgical patty manager according to claim 1, further comprising a gripping tool releasably coupled to one of the first tray and the second tray.

10. The surgical patty manager according to claim 9, further comprising a gripping tool retaining device, the gripping tool retaining device being affixable to the one of the first tray and the second tray and being arranged to releasably retain the gripping tool.

11. The surgical patty manager according to claim 1, wherein the first tray includes a string guide adjacent the dispensing region, the string guide defining a channel extending along at least a portion of the periphery of the dispensing region and includes a channel extending longitudinally along a portion of the first tray.

12. The surgical patty manager according to claim 11, further comprising a protrusion extending partially over a portion of the string guide.

13. The surgical patty manager according to claim 1, wherein the first tray includes a first portion releasably engageable with a second portion.

14. The surgical patty manager according to claim 13, wherein the second portion is positionable within the first portion.

15. A surgical patty manager for retaining a plurality of surgical patties, comprising:

a first tray defining a plurality of dispensing regions, each dispensing region including a patty retention element and a dispensing indicator located therein, each dispensing region adapted to secure an unused surgical patty therein;

the first tray defining a string guide adjacent each dispensing region, the string guide defining a channel extending along at least a portion of the periphery of the dispensing region and a protrusion extending partially over a portion of the string guide;

a plurality of unused surgical patties retained in the plurality of dispensing regions by the corresponding patty retention element, each of the unused surgical patties having an associated string routed through the string guide; and a second tray movably coupled to the first tray, the second tray defining a plurality of recovery regions each corresponding to one of the plurality of dispensing regions, each recovery region including a patty retention element, and a recovery indicator located therein, each recovery region adapted to secure a used surgical patty therein.

16. The surgical patty manager according to claim 15, wherein each recovery-indicia is substantially similar to a corresponding dispensing indicia.

17. The surgical patty manager according to claim 15, further comprising a separator sheet positionably within a portion of the first tray.

18. The surgical patty manager according to claim 15, wherein the string guide includes a channel extending longitudinally along a portion of the first tray.

19. The surgical patty manager according to claim 15, further comprising a protrusion extending partially over a portion of the string guide.

20. A surgical patty manager for retaining a plurality of surgical patties, comprising:

a first tray comprising a plurality of dispensing regions, each dispensing region comprising a patty retention element and a dispensing indicator located therein;

the first tray defining a string guide and a protrusion extending partially over a portion of the string guide adjacent each dispensing region the string guide defining a first channel extending longitudinally along a portion of the first tray, and a second channel extending along at least a portion of the periphery of the dispensing region;

a plurality of unused surgical patties retained in the plurality of dispensing regions by the corresponding patty retention element, each of the unused surgical patties having an associated string routed through the string guide; and a second tray hingedly coupled to the first tray, the second tray foldable about a hinge onto the first tray into a folded configuration, the second tray comprising a plurality of recovery regions, each recovery region corresponding to one of the dispensing regions in the plurality of dispensing regions, each recovery region comprising a patty retention element and a recovery indicator located therein; and the recovery indicator being at least partially concealed when a surgical patty is retained within the patty retention element.

21. The surgical patty manager according to claim 20, further comprising a gripping tool releasably coupled to one of the first tray and the second tray.

22. The surgical patty manager according to claim 21, further comprising a gripping tool retaining device, the gripping tool retaining device being affix able to the one of the first tray and the second tray and being arranged to releasably retain the gripping tool.

* * * * *